US00PP14060P39

(12) United States Plant Patent
Noodelijk

(10) Patent No.: US PP14,060 P3
(45) Date of Patent: Aug. 12, 2003

(54) CHRYSANTHEMUM PLANT NAMED 'AMOR WHITE'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/734,606

(22) Filed: Dec. 13, 2000

(65) Prior Publication Data

US 2002/0148023 P1 Oct. 10, 2002

(51) Int. Cl.[7] ..... A01H 5/00

(52) U.S. Cl. ..... Plt./287

(58) Field of Search ..... Plt./294, 287

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'Amor White' characterized by its medium sized blooms with white ray florets and prolific branching; natural season flower date September 4–9; blooming for a period of 7 weeks.

3 Drawing Sheets

RELATED CULTIVARS

'Amor White' is related to 'Amor' (Ser. No. 09/734,607). 'Amor White' is a color mutant of 'Amor'.

BACKGROUND OF THE INVENTION

'Amor White' is a product of a breeding and selection program that had the objective of finding color mutants of 'Amor'. The new plant of the present invention comprises a new and distinct cultivar of Chrysanthemum plant that is a natural occurring sport of a parent Chrysanthemum named 'Amor'. A comparison with parent chrysanthemum 'Amor' is also made in this application. The new cultivar was discovered as a sport in September, 1998 by Rob Noodelijk in a controlled environment (greenhouse) in Rijsenhout, Holland. The first act of asexual reproduction of 'Amor White' was accomplished when vegetative cuttings were taken from the initial selection in October, 1998 in Rijsenhout, Holland. The new cultivar has been found to retain its distinctive characteristics through successive propagations.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
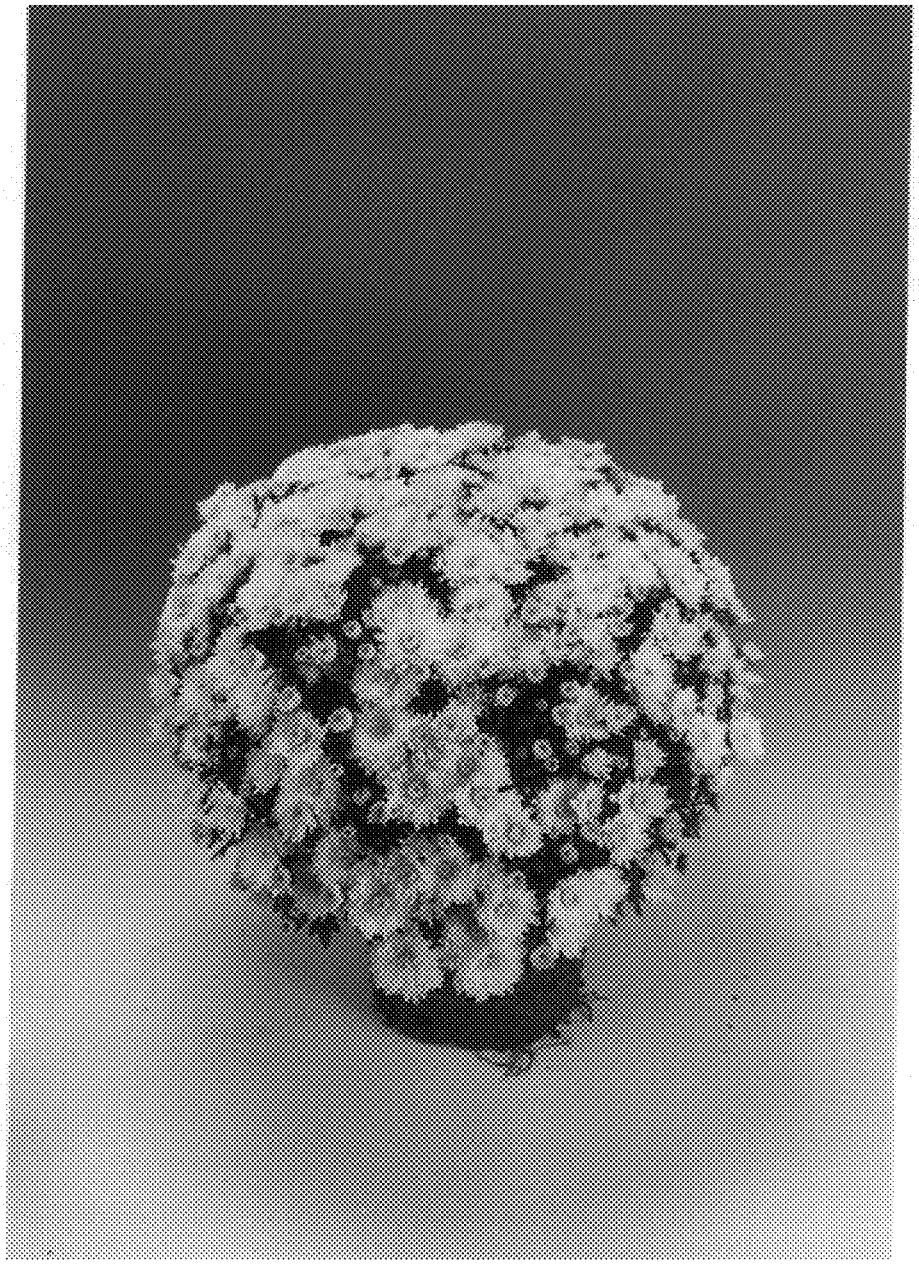
FIG. 1 shows a plant of the cultivar in full bloom.
Figure 2:
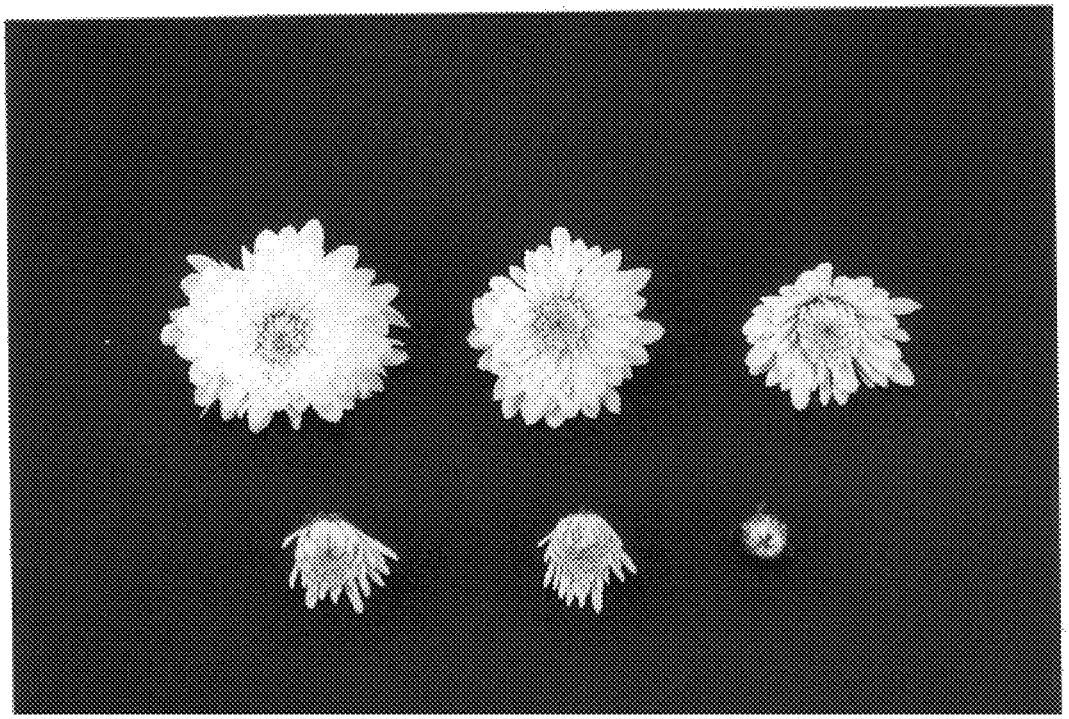
FIG. 2 shows the various stages of bloom of the new cultivar.
Figure 3:
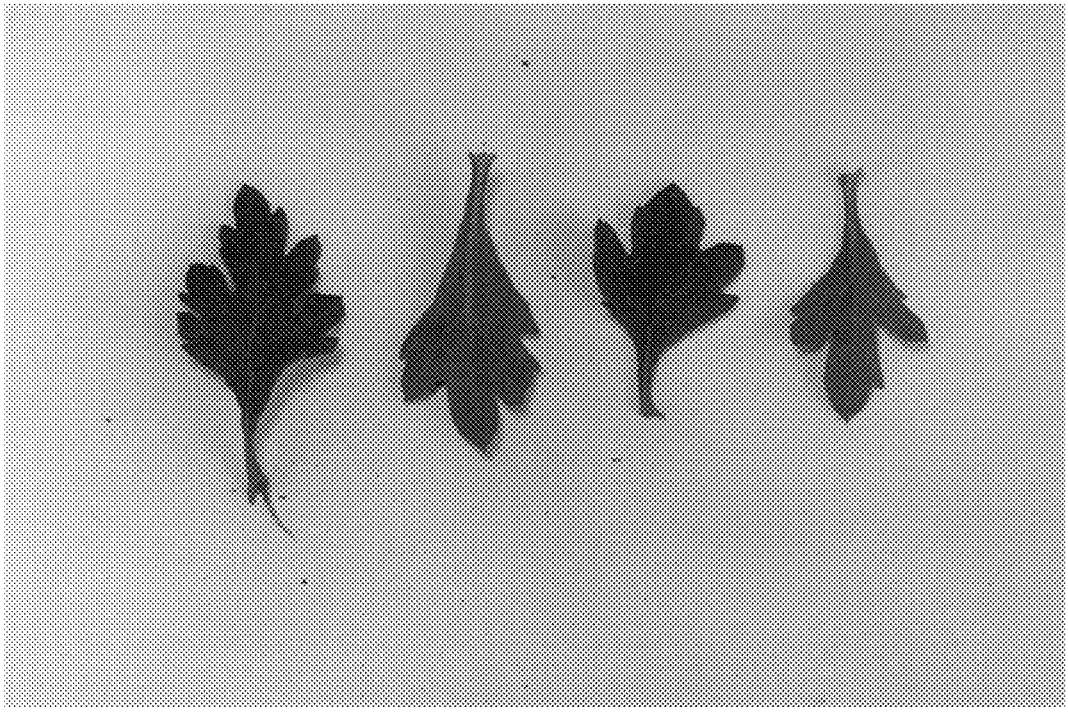
FIG. 3 shows the various stages of foliage and petiole of the new cultivar.

This new variety of Chrysanthemum is of the botanical classification *Chrysanthemum morifolium.* The observations and measurements were gathered from plants grown out door in Rijsenhout, Holland under natural day length and temperature and planted week 22 in 1999 and 2000. The natural blooming date of this crop was September 4–9 (week 36). The average height of the plants was 32–38 cms. No growth retardants were used. No tests were done on disease or insects resistance or susceptibility. No tests were done on cold or drought resistance. This new variety produces medium sized blooms with white ray florets and a yellow center blooming for a period of 7 weeks.

When 'Amor' and 'Amor White' and are being compared the following differences and similarities are noticed: The differences of 'Amor' and 'Amor White' are (1) Flower color and (2) Vigour. All other characteristics of 'Amor' and 'Amor White' are similar.

(1) Flower color. 'Amor White' is a sport of 'Amor', bearing white ray-florets instead of pink ray-florets.

(2) Vigour: The plants of 'Amor White' tend to be a little more vigorous.

The following is a description of the plant and characteristics that distinguish 'Amor White' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Table 1: Botanical Description of Cultivar 'Amor White'.

Bud:
- *Size.*—Medium;cross-section 1.2 cm, height 1.0 cm.
- *Outside color.*—Yellow 8 D.
- *Involucral bracts.*—2 rows, length 7 mm, width 3 mm.
- *Involucral bracts among disc-florets.*—Not present.
- *Involucral bracts color.*—Green 138 B.

Bloom:
- *Type.*—Decorative.
- *Height.*—High, 3.0–3.5 cm.
- *Size.*—Medium.
- *Fully expanded.*—5.0–5.5 cm.

*Borne* (*number of blooms per branch*).—Upper and lower portion plural blooms per branch (Approx. 5 blooms per branch).
*Performance on the plant.*—7 weeks.
*Seeds* (*if crossed*).—Produced in small quantities, ovate. Grey-brown 199 A, 1½ mm in length.
*Fragrance.*—Typical chrysanthemum, slight.

Color:
*Center of the flower.*—Immature Yellow 8 C. Mature Yellow 8 C.
*Color of upper surface of the majority of the ray-florets.*—White 155D.
*Color of the lower surface of the majority of the ray-florets.*—White 155D.
*Tonality from distance.*—A mounded decorative garden mum with white blooms with a yellow center.
*Color of the upper surface of the flowers after aging of the plant.*—White 155D.

Ray florets:
*Texture.*—Upper and under side smooth.
*Number.*—200–230.
*Cross-section.*—Concave.
*Longitudinal axis of majority.*—Incurved to straight.
*Length of corolla tube.*—Medium, 0.9–1.1 cm.
*Ray-floret margin.*—Entire.
*Ray-floret length.*—2.5–2.8 cm.
*Ray-floret width.*—0.4–0.6 cm.
*Ratio length/width.*—High.
*Shape of tip.*—Pointed.

Reproductive organs:
*Stamen.*—Not present.
*Pollen.*—Not present.
*Styles* (*present in ray-florets*).—Thin.
*Style color.*—Yellow-green 144 A.
*Style length.*—4 mm.
*Stigma color.*—Yellow-green 144 A.
*Stigma width.*—1 mm.
*Ovaries.*—Enclosed in calyx.

Plant:
*Shape.*—Grown as a spray-type pot-mum, outdoor mounded and round.
*Growth habit.*—Spreading.
*Growth rate.*—Moderate.
*Height.*—32–38 cm.
*Width.*—35–40 cm.
*Stem color.*—Green 138 B.
*Stem strength.*—Strong.
*Stem brittleness.*—Present.
*Stem anthocyanin coloration.*—Absent.
*Length of lateral branch.*—From top to bottom 14–15 cm.
*Lateral branch color.*—Green 138 B.
*Lateral branch, attachment.*—Weak.
*Branching* (*average number of lateral branches*).—Mounding and prolific with 8–10 breaks after pinching.
*Peduncle length.*—4.0–4.5 cm.
*Peduncle color.*—Green 138 B.
*Natural season blooming date.*—September 4–9.

Foliage:
*Color of mature leaves.*—Upper side green 138 A. Under side green 138 B.
*Color of immature leaves.*—Upper side green 138 B. Under side green 138 B.
*Size.*—Small; length 6 cm, width 5 cm.
*Quantity* (*number per lateral branch*).—12–14.
*Shape.*—Oval.
*Texture upper side.*—Glabrous.
*Texture under side.*—Pubescent.
*Ribs and veins upper side.*—Ribs and veins well developed.
*Venation arrangement.*—Palmate.
*Shape of the margin.*—Serrate.
*Shape of base of sinus between lateral lobes.*—Acute.
*Margin of sinus between lateral lobes.*—Diverging.
*Shape of base.*—Asymmetric.
*Apex.*—Mucronate.

TABLE 2

Differences with the comparison varieties (when grown under the same conditions)

| | 'AMOR WHITE' | 'AMOR' |
|---|---|---|
| Color of ray-florets | White 155D | Red-purple 74C |
| Length of lateral branch | 14–15 cm | 12–13 cm |
| Plant height | 32–28 cm | 32–26 cm |

I claim:

1. A new and distinct variety of Chrysanthemum plant as described and illustrated.

* * * * *